United States Patent
Civelli et al.

(10) Patent No.: US 6,326,156 B1
(45) Date of Patent: *Dec. 4, 2001

(54) METHOD OF IDENTIFYING COMPOUNDS HAVING ANTIEPILEPTIC ANTICONVULSANT OR ANXIOLYTIC ACTIVITIES

(75) Inventors: Olivier Civelli, Irvine, CA (US); James Richard Martin, Therwil; Frederick Monsma, Riehen, both of (CH); Jean-Luc Moreau, Rixheim (FR); Hans-Peter Nothacker, Schliengen; Rainer Reinscheid, Freiburg, both of (DE)

(73) Assignee: Hoffmann-La Roche Inc., Nutley, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 31 days.

(21) Appl. No.: 08/868,355

(22) Filed: Jun. 3, 1997

(30) Foreign Application Priority Data

Jun. 13, 1996 (EP) .................................................. 96109462

(51) Int. Cl.$^7$ ........................ G01N 33/53; G01N 33/566; G01N 33/567
(52) U.S. Cl. ............................. 435/7.1; 435/7.2; 435/7.21
(58) Field of Search ............................ 435/7.1, 7.2, 7.21; 514/2, 12, 13

(56) References Cited

U.S. PATENT DOCUMENTS

| 5,463,105 | 10/1995 | Schohe et al. . |
| 5,476,933 | * 12/1995 | Keana et al. . |
| 5,658,783 | * 8/1997 | Grandy et al. . |
| 5,703,101 | * 12/1997 | Rose . |

FOREIGN PATENT DOCUMENTS

| 612 845 | 8/1994 | (EP) . |
| 187388 | 9/1983 | (HU) . |
| T/67677 A | 9/1993 | (HU) . |
| WO 94/28132 | 8/1994 | (WO) . |
| WO 97/07208 | 2/1997 | (WO) . |
| WO 97/07212 | 2/1997 | (WO) . |

OTHER PUBLICATIONS

Zezula et al., *Neurosci.*, vol. 25, pp. 771–795, 1988 (Abstract only).*
Ono et al., *Orzneimittel–Forschung*, vol. 37, pp. 384–388 (Abstract only), 1987.*
Rocha et al., *Brain Res.*, vol. 612, pp. 247–252, 1993.*
Jenck, et al., Orphanin FQ acts as an anxiolytic attenuate behavioral responses to stress, Proc. Natl. Acad. Sci., vol. 94, pp. 14854–14858 (1997).
Reinscheid, et al., "Structure–Activity Relationship Studies on the Novel Neuropeptide Orphanin FQ", J. Biol. Chem., vol. 271, No. 24, pp. 14163–14168 (1996).
Bunzow et al., Molecular cloning and tissue distribution of a putative member of the rat opioid receptor gene family that is not a $\mu$, $\delta$ or $\kappa$ opioid receptor type, FEBS Letters, vol. 347 pp. 284–288 (1994).
Chen et al., Molecular cloning, tissue distribution and chromosomal localization of a novel member or the opioid receptor gene family, FEBS Letters, vol. 347. pp. 279–283 (1994).
Fukuda et al., cDNA cloning and regional distribution of a novel member of the opioid receptor family, FEBS Letters, vol. 343 pp. 42–46 (1994).
Mollereau et al., ORL1, a novel member of the opioid receptor family Cloning, functional expression and localization, FEBS Letters, vol. 341 pp. 33–38 (1994).
Wang et al., cDNA cloning of an orphan opiate receptor gene family member and its splice variant, FEBS Letters, vol. 348, pp. 75–79 (1994).
Lachowicz et al., Molecular Cloning of a Novel G Protein–Coupled Receptor Related to the Opiate Receptor Family, Journal of Neurochemistry, vol. 64, No. 1 pp. 34–40 (1995).
Nishi et al., Structure and Chromosomal Mapping of Genes for the Mouse $\kappa$–Opioid Receptor and an Opiod Receptor Homologue (MOR–C), Biochemical and Biophysical Research Communications, vol. 205, No. 2, pp. 1353–1357 (1994).
Wick et al., Isolation of a novel cDNA encoding a putative membrane receptor with high homology to the cloned $\mu$, $\delta$, and $\kappa$ opioid receptors, Molecular Brain Research, vol. 27 pp. 37–44 (1994).
Meunier et al., Isolation and structure of the endogenous agonist of opioid receptor–like ORL$_1$ receptor, Nature, vol. 377, pp. 532–535 (1995).
Reinscheid et al., Orphanin FQ: A Neuropeptide That Activates an Opioidlike G Protein–Coupled Receptor, Science, vol. 270, pp. 792–794 (1995).
Vaughan et al., Increased by the ORL$_1$ receptor (opioid receptor–like$_1$) ligand, nociceptin, of inwardly rectifying K conductance in dorsal raphe nucleus neurones, British Journal of Pharmacology vol. 117, pp. 1609–1611 (1996).
David Julius, Home for an orphan endorphin, Nature, vol. 377, pp. 476 (1995).
Zhang et al., Identification of Dynorphins as Endogenous Ligands for an Opioid Receptor–like Orphan Receptor, The Journal of Biological Chemistry, vol. 270, No. 39, pp. 22772–22776 (1995).

* cited by examiner

*Primary Examiner*—Gary L. Kunz
*Assistant Examiner*—Stephen Gucker
(74) *Attorney, Agent, or Firm*—George W. Johston; Dennis P. Tramaloni; F. Aaron Dubberley

(57) ABSTRACT

The present invention relates to a method of screening for a therapeutically useful compound which comprises testing an LC132 receptor agonist in a screening assay for psychiatric and/or neurological disorders. More particularly, the screening method is based on contacting an LC132 receptor with an agent suspected of being an agonist of the LC132 receptor function, followed by the detection of the binding and/or the agonist activity of the compound and then testing of an agent with LC132 agonist activity in an antiepileptic, anticonvulsant or anxiolytic screening assay.

10 Claims, No Drawings

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 17 amino acids
      (B) TYPE: amino acid
      (D) TOPOLOGY: linear (ii) MOLECULE TYPE: peptide (iii) HYPOTHETICAL: NO (xi) SEQUENCE DESCRIPTION: SEQ ID NO:1:

```
Phe Gly Gly Phe Thr Gly Ala Arg Lys Ser Ala Arg Lys Leu Ala Asn
1               5                   10                  15
Gln
```

METHOD OF IDENTIFYING COMPOUNDS HAVING ANTIEPILEPTIC ANTICONVULSANT OR ANXIOLYTIC ACTIVITIES

The present invention relates to a screening method comprised of testing an LC132 receptor agonist in screening assays for neurological and/or psychiatric disorders. More specifically, the screening method is based on bringing an LC132 receptor in contact with an agent suspected of acting as an agonist of LC132 receptor function followed by the detection of the binding and/or the agonist activity of the compound and then the testing of an agent with LC132 agonist activity in an antiepileptic, anticonvulsant and/or anxiolytic screening test to demonstrate therapeutically relevant activity in these disorders.

At present, benzodiazepine receptor agonists (e.g., alprazolam, diazepam, lorazepam) still represent the predominant treatment in clinical medicine for anxiety disorders, especially acute anxiety. Since benzodiazepine receptor agonists have anticonvulsant properties, some are also used as antiepileptic drugs. More recently, other drug classes have found clinical use in the treatment of anxiety disorders, for example selective serotonin reuptake inhibitors (e.g., fluoxetine) and buspirone. Treatment of epilepsies is currently dominated by drugs such as carbamazepine, phenytoin, valproate, ethosuximide, and phenobarbital. As discussed below, the available drugs used in the pharmacological treatment of anxiety, epilepsies, and convulsions are not optimal.

Anxiety is a physiologic phenomenon that acts as a warning signal for a real or potential danger. Anxiety becomes pathologic when it occurs in the absence of any real danger or when the intensity of the emotion is exaggerated. Both physiologic and pathologic anxiety can be life-threatening when occurring in the face of pre-existing organic disorders and may create or perpetuate various physiologic dysfunctions. The diverse anxiety disorders represent relatively common psychiatric disorders with an estimated combined prevalence within the general population of about 4–8 percent. The immediate relief provided by benzodiazepine receptor agonists in treating anxiety disorders is well documented. Although the efficacy of these drugs appears to be maintained over a long period, a series of issues arise when treatment is administered for more than several weeks. Although undesirable side-effects can largely be avoided by optimising dosage of benzodiazepine receptor agonists for the individual patient, doses required for severe cases of anxiety and epilepsies as well as for reducing pathologic muscle tone frequently depress vigilance to a level that disturbs intellectual function and reduces attention and precision for various skills (operation of machines, car driving). The individual sensitivity to this oversedation varies greatly. Muscle relaxation may result in blurred speech and disturbed gait, especially in elderly patients. Behavioral disinhibition may occur at higher doses and even at normal doses in individuals having minimal experience with centrally active drugs. Problems can also occur due to long-lasting exposure to benzodiazepine receptor agonists. One such is the development of tolerance to a therapeutic effect. Loss of antiepileptic efficacy occurs in a fair proportion of patients (manifested as escape phenomena). Physical dependence manifested as drug discontinuation symptoms following abrupt withdrawal is a function of duration of drug exposure, dose, duration of action of the drug, and the personality of patients. In marked contrast to anxiolytics acting via benzodiazepine receptor agonism (which exhibit anticonvulsant, muscle relaxant, and sedative/hypnotic effects), the azaspirodecanedione buspirone presents only anxiolytic activity. It has been hypothesized that the mechanism of action of buspirone involves partial agonism at the serotonin1A receptor. Advantages of buspirone include less sedation, less psychomotor impairment in conjunction with ethanol consumption, reduced physical dependence, and a much lower abuse liability than for benzodiazepine receptor full agonists. However, the long latency in the onset of anxiolytic activity is a pronounced difference to classic benzodiazepine tranquilizers which act rapidly. In addition, there are possible problems in treatment compliance for buspirone and questions about efficacy in patients previously treated with benzodiazepine receptor agonists or exhibiting severe anxiety. Buspirone is not only a valuable addition to the medical armamentarium whose place is gradually becoming more clearly defined, but also very important from the theoretical standpoint insofar as it is the first anxiolytic to meet the rigorous clinical efficacy and safety standards of modern. In view of the mechanism of action of selective serotonin reuptake inhibitors (SSRIs), it appears that the resulting increased availability of the neurotransmitter serotonin within the synaptic cleft is responsible for the pharmacological effects of this drug class. However, onset of the therapeutic action of SSRIs is slow, usually requiring at least several weeks. Although originally developed and predominantly used as antidepressants, SSRIs have been increasingly used in treating panic disorder, e.g. fluoxetine or obsessive-compulsive disorder, e.g. fluvoxamine. SSRIs are generally well tolerated, nonetheless, common adverse effects for compounds in this class include nervousness, tremor, dizziness, headache, insomnia, sexual dysfunction, nausea, and diarrhea. In addition, the tricyclic antidepressant clomipramine, which is a potent nonselective serotonin reuptake inhibitor, is approved for treatment of obsessive compulsive disorder [e.g. see: Martin and Haefely, in "Principles of Pharmacology, Eds. Munson et al., Chapman & Hall, N.Y., 1995, pp. 243–277].

Epilepsy is a neurologic disorder which affects up to about 1 percent of the population. This chronic condition is characterised by recurrent spontaneous seizures not caused by active cerebral disease. Seizures are sudden, involuntary, time-limited alterations in behavior associated with excessive discharges of cerebral neurons. Today the epilepsies are usually classified according to the main seizure type presented by the patient (a given patient may have more than one seizure type but one is usually more frequent than the others and is used as basis for classification). A practical advantage of the classification by seizure type is that it allows, to a certain degree, prediction of responsiveness to therapeutic alternatives. Generally, only about half of the patients will have their seizures satisfactorily controlled with antiepileptic drugs; the remaining half will be divided into patients having occasional seizures and patients who have uncontrolled seizures and/or unacceptable adverse effects from antiepileptic medications. Furthermore, the drugs currently used frequently cause side effects. There are multiple etiologies for seizures and the origin often remains obscure, thus, antiepileptics as well as other drugs exhibiting anticonvulsant effects are important therapeutically. (e.g. see: Lloyd and Gillenwater, in "Principles of Pharmacology, Eds. Munson et al., Chapman & Hall, N.Y., 1995, pp. 363–398).

Previously, a seventeen amino-acid-long peptide (F-G-G-F-T-G-A-R-K-S-A-R-K-L-A-N-Q) (SEQ ID NO: 1) called orphanin FQ or nociceptin has been isolated from rat brain (Meunier et al., Nature 377: 532–535, 1995) and from porcine hypothalami (Reinscheid et al., Science 270:

792–794, 1995). The amino acid sequence of orphanin FQ is identical with that of nociceptin and will be thereafter referred to as OFQ. Julius (Nature 377: 476, 1995) discusses the OFQ discovery noting that this peptide shares greatest sequence similarity with dynorphin A, one of five established endogenous ligands for opioid receptors. OFQ inhibits adenylate cyclase in CHO(LC132$^+$) cells in culture and induces hyperalgesia when administered intracerebroventricularly to mice (Meunier et al., loc. cit.). The pattern of results indicate that this heptadecapeptide is an endogenous agonist of the LC132 receptor and it appears to have pro-nociceptive properties. Reinscheid et al. (loc. cit.) describe that when injected intracerebroventricularly in mice, OFQ decreased locomotor activity and induced hyperalgesia in the tail-flick test (but not in the hot-plate test). It was concluded that OFQ may act as a brain neurotransmitter to modulate nociceptive and locomotor behavior.

Vaughan and Christie (Br. J. Pharmacol. 177: 1609–1611, 1996) investigated the actions of OFQ on the membrane properties of rat dorsal raphe nucleus neurons using whole-cell patch clamp recording in brain slice. Consistent with the reported presence of the LC132 receptor mRNA in dorsal raphe neurons (Lachowicz et al., J. Neurochem. 64: 34–40, 1995) and G-protein-mediated coupling of cloned LC132 receptors to the activation of K channels (Zhang and Yu, J. Biol. Chem. 270: 22772–22776, 1995), it was found that the LC132 receptor ligand nociceptin potently and efficaciously increased inwardly rectifying K conductance in dorsal raphe neurons.

It is demonstrated herein that agonists of the LC132 receptor like OFQ have effects in animal models of psychiatric and neurological disorders (predicting therapeutic efficacy in patients), especially, but not limited to treatment of anxiety disorders, epilepsies, and convulsions. This determination has allowed applicant to develop methods and protocols by which useful substances can be identified which provide both therapeutically useful compounds and/or lead compounds to be used in the discovery of therapeutically useful compounds. Accordingly, the present invention relates to methods of screening for a therapeutically useful compound which comprise of testing an LC132 receptor agonist in a screening assay for psychiatric and/or neurological disorders, especially in an antiepileptic, anticonvulsant, or anxiolytic screening test.

In a preferred embodiment, the method of screening for a therapeutically useful compound comprises of testing an LC132 receptor agonist in a psychiatric and/or neurological disorder screening assay. Preferably, the method comprises contacting an LC132 receptor with an agent suspected of having LC132 receptor agonist activity and detection of the LC132 receptor-agent binding and/or the determination of the LC132 receptor agonist activity followed by testing of an agent having agonist activity in a psychiatric and/or neurological disorder screening assay, namely an antiepileptic, anticonvulsant or an anxiolytic screening assay.

The term "LC132 receptor" or "LC132 receptor protein" refers to the native receptor protein and derivatives thereof. This receptor or its derivatives from different animal species has had in the literature several names, the most commonly used being ORL$_1$. The LC132 receptor, an orphan receptor whose human and murine complementary DNAs have recently been characterised, structurally resembles to opioid receptors (Mollereau et al., FEBS Lett. 341: 33–38, 1994; Fukuda et al, FEBS Lett. 343: 42–46, 1994; Chen et al., FEBS Lett. 347: 279–283, 1994; Bunzow et al., FEBS Lett. 347: 284–288, 1994; Wang et al., FEBS Lett. 348: 75–79, 1994; Lachowicz et al., loc. cit.; Nishi et al., Biochem. Biophys. Res. Commun. 205: 1353–1357, 1994 and Wick et al., Molec. Brain Res. 27: 37–44, 1995). The LC132 receptor bioactivity is characterised by its high-affinity binding of OFQ and is negatively coupled with adenylate cyclase (Meunier et al., loc. cit.; Reinscheid et al., 1995, loc. cit.).

Ordinarily, preferred LC132 receptors derivatives have an amino acid sequence having at least 80% amino acid sequence identity with the corresponding human LC132 receptor amino acid sequence, preferably at least 90% and most preferably at least 95% and are characterised in that they are capable of binding to OFQ with high affinity. A particularly advantageous embodiment of the assay method comprises the use of the native human LC132 receptor protein.

The term "LC132 receptor protein" also comprises derivatives of naturally or non-naturally occurring receptor proteins and related proteins comprising at least partial protein sequence capable of binding to the OFQ peptide, i.e. proteins in which one or more of the amino acids of the natural LC132 receptor or its fragments have been replaced or deleted without loss of binding activity. Such derivatives may be produced by known methods of peptide chemistry or by recombinant DNA technology. The term "LC132 receptor protein" also comprises derivatives which may be prepared from the functional groups occurring as side chains on the residues or the N- or C-terminal groups, by means known in the art. These derivatives may include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl- or threonyl residues) formed with acyl moieties.

The LC132 (opioid-like) orphan receptor was recently identified on the basis of close homology with the predicted amino acid sequence opioid receptors (Mollereau et al, loc. cit.; Bunzow et al., loc. cit.; Lachowicz et al., loc. cit.). When LC132 receptors were expressed in heterologous systems, e.g. CHO cell lines, etorphine and dynorphin A weakly inhibited cyclic AMP formation, but other opioids were inactive. The heptadecapeptide OFQ has been identified as a potent and efficacious endogenous agonist of the LC132 receptor (Meunier et al., loc. cit., Reinscheid et al. (1995), loc. cit.). The LC132 transcripts are expressed in several areas of the central nervous system that are known to be involved in pain regulation, including the hypothalamus, brainstem and spinal cord dorsal horn (Julius, loc. cit.).

The expression of the LC132 receptor protein and derivatives thereof can be achieved by conventional recombinant DNA technology. Such techniques are explained in the literature (see e.g. Sambrook, Fritsch & Maniatis, "Molecular Cloning. A Laboratory Manual", Cold Spring Harbor Laboratory, N.Y., 1989 and Ausubel et al., "Current Protocols in Molecular Biology", Green Publishers Association & Wiley Interscience, 1987). Further, DNA molecules or fragments thereof encoding complete or partial LC132 proteins may be obtained with the polymerase chain reaction (PCR) technique. Nucleic acid sequences encoding the LC132 receptor may be expressed using a wide variety of host/vector combinations. Useful expression vectors may consist of segments of chromosomal, non-chromosomal and synthetic nucleic acid sequences. Examples of such vectors are viral vectors, such as the various known derivatives of SV40, bacterial vectors, such as plasmids from *E. coli*, phage DNAs, such as λ phage derivatives, M13 and other filamentous single-stranded DNA phages, as well as vectors useful in yeasts, such as derivatives of the $2\mu$ plasmid, vectors useful in eukaryotic cells more preferably vectors useful in animal cells, such as those containing SV40, adenovirus and/or retrovirus derived DNA sequences.

The host cell used for the expression of LC132 receptor encoding nucleic acid sequences may be selected from a variety of known hosts. A large number of hosts are available for example from The American Type Culture Collection (ATCC). Preferred hosts for the LC132 expression are mammalian cells such as CHO cells. The preparation of LC132 receptor expressing cell lines is known in the art and described for example by Reinscheid et al. (1995, loc. cit.).

The term "LC132 receptor agonists" refers to compounds capable of binding to the LC132 receptor and thereby modulating the LC132 receptor function, i.e. inhibiting forskolin-stimulated adenylyl cylase activity in a cell transformed with a vector capable of expressing the LC132 receptor. Exemplary agonists are high affinity ligands, preferably with $IC_{50}$ values of less than 1 $\mu M$, e.g. OFQ or derivatives thereof.

The term "contacting an LC132 receptor with an agent suspected of having LC132 receptor agonist activity" may comprise the following features: An LC132 receptor protein, preferably a human LC132 receptor protein, is bound in appropriate buffer conditions to a solid phase. The solid phase is usually poly(vinylchloride), but may be other polymers such as cellulose, polyacrylamide, nylon, polystyrene or polypropylene. The solid supports may be in the form of tubes, beads, discs or micro plates, or any other surfaces suitable for conducting an assay, and which on passive binding of the LC132 receptor, exposes the high affinity receptor binding site. After washing, an agent suspected of binding to the LC132 receptor and/or of having LC132 receptor agonist activity may be added in an appropriate buffer solution.

The preferred way of preparation of the LC132 receptor is characterised by the transfection of a mammalian cell line, e.g. a CHO cell line, with a vector containing a nucleic acid sequence encoding the LC132 receptor followed by the expression of the receptor protein. Purified membrane containing the receptor protein may then be bound to the solid surface as described above and incubated with agents suspected of being an LC132 receptor agonist. These methods are known in the art and are described e.g. by Reinscheid et al., loc. cit. In this case the method according to the invention comprises (a) providing cell membranes containing LC132 receptors, (b) contracting the membranes with a compound suspected of being an LC132 receptor agonist and (c) determining whether the compound binds to the LC132 receptor and exerts agonist specific activity followed by a psychiatric and/or neurological disorder screening assay.

The detection of binding of the agent suspected of being an agonist to the LC132 receptor may be done by direct labelling of the agent or by labelling of a competitive agent like OFQ. The agent or the competitive agent may be marked for example with a radioactive label. A preferred embodiment is described by Reinscheid et al. (1995, loc. cit.) and also in EXAMPLE 1.

The pharmacological characterisation of the LC132 receptor agonist activity may be determined by the extent of inhibition of the forskolin-stimulated cAMP accumulation in the host cells (e.g. CHO cells) transfected with a vector capable of expressing the LC132 receptor. Concentrations of cAMP may be determined as described by Reinscheid et al. (1995, loc. cit.) or by other methods known in the art. A particular preferred embodiment of the present invention comprising the determination of LC132 receptor agonist activity is described in EXAMPLE 1.

LC132 receptor agonists may then be further characterised by any known or coventional psychiatric and/or neurological disorder screening assay. The term "psychiatric and/or neurological screening assay" refers to, but is not limited to, anxiolytic, antiepileptic and/or anticonvulsant screening assays. These assays are known in the art as described below:

Anxiety tests (Martin & Haefely, cit. loc.). A large number of animal models have been developed in the attempt to predict the anxiolytic activity of novel compounds in man. Many of these paradigms evaluate animal behavior in a so-called "conflict" situation, i.e. a behavioral response is simultaneously under the influence of two opposing motivational states such as approach and avoidance tendencies. Probably the best known model is the conditioned punishment conflict paradigm in which animals are trained to voluntarily exhibit a certain response (e.g. pressing a lever) in order to receive a reward (e.g. food for a hungry animal). Once the animals exhibit a constant rate of lever-press responding, then short periods are introduced (usually signalled by visual or acoustic signals) during which lever pressing is simultaneously rewarded by food and punished by mild electrical foot shock. Animals exhibit a markedly reduced response rate during these conflict periods, which are also characterised by various overt signs of emotionality. The characteristic effect of benzodiazepine receptor agonists, for example the anxiolytic diazepam, is the disinhibition of punished behavior (resulting in an increase in the rate of responding under punishment) at doses that fail to disrupt unpunished responding. Furthermore, these same active drugs produce an anxiolytic-like effect in the absence of actual punishment, i.e. when the rate of lever pressing is reduced by conditioned fear of punishment. The conflict task does not require conditioned behavioral responses: naive thirsty animals can be offered the opportunity to drink, with drinking punished via contact with an electrified spout. Such punishment-suppressed drinking is disinhibited dose-dependently by benzodiazepine receptor agonists (e.g., diazepam). Exploratory activity can likewise be decreased by contingent punishment and released by treatment with known anxiolytics. Conflict models without punishment are based on the presence of the natural opposing motivational states, on the one hand the tendency to explore and, on the other hand, fear of a novel environment (e.g. dark-light chamber task, elevated plus-maze, consumption of unfamiliar food or normal food in an unfamiliar environment, social interaction between animals unfamiliar with each other). While it is obvious to ascribe the behavioral disinhibitory effect of benzodiazepine receptor agonism in these experimental situations to an anxiolytic-like action, their effect can also be interpreted as a general reduction of the influence of aversive factors or even to an impaired ability to withhold innate or conditioned responses. An anti-frustration effect resulting from benzodiazepine receptor agonism is suggested by the increase of responding which is maintained by response-contingent reward in the situation in which the reward is reduced or omitted. Electrical stimulation of the periaqueductal gray area of the midbrain via chronically implanted electrodes in animals is aversive and elicits a number of emotional reactions; benzodiazepine receptor agonists increase the aversive threshold. States of acute anxiety characterised by behavioral and physiological symptoms (cardiovascular, endocrine) can be induced by chemicals known to be anxiogenic in man, e.g. convulsants such as pentylenetetrazol, inverse agonists at the benzodiazepine receptor agonists administered in subconvulsive doses, or even abrupt drug withdrawal after chronic treatment with high doses of sedatives. Ultrasonic distress cries by rat pups acutely separated from their mothers are decreased by benzodiazepine receptor agonists. The pharmacological specificity of benzodiazepine receptor agonists in the above paradigms is impressive, whereas antidepressants, analgesics, and antipsychotics are all relatively ineffective.

Antiepilepsy/anticonvulsant tests (Martin & Haefely, loc. cit.). Benzodiazepine receptor agonists are among the most potent drugs known for use in preventing or abolishing seizures in animals induced acutely by chemicals administered systemically (e.g. pentylenetetrazol, bicuculline, picrotoxin, inhibitors of GABA biosynthesis, penicillin, local anesthetics, inhibitors of acetylcholinesterase), applied locally on the cortical surface or into the ventricular system (cardiac glycosides, the glutamate receptor stimulant NMDA), or applied chronically into the cortex (focal aluminium or cobalt epilepsy). They are also effective in protecting against hyperbaric seizures and from seizures developing after chronic intermittent electrical stimulation in the limbic system beginning at a subthreshold intensity (kindled seizures). Electroconvulsive seizures are also prevented by most (but not all) benzodiazepine receptor agonists, although at doses considerably higher than those found to block chemically-induced seizures. Various genetic models of epilepsy (a petit mal-like phenotype in rats, seizures induced by acoustic stimulation in genetically-prone mouse strains or myoclonic seizures induced by photic stimulation in genetically-prone baboons) respond to benzodiazepine receptor agonists. Thus, benzodiazepine receptor agonists are effective in all current animal epilepsy models which are predictive of efficacy in most forms of human epilepsy or convulsive states. Consistent with their broad anticonvulsant activity, benzodiazepine receptor agonists prevent or suppress epileptiform electric activity induced by various procedures (convulsants, ionic composition) in brain slices maintained in vitro, particularly hippocampal slices. They also reduce the neuronal afterdischarges induced in various brain regions by electrical stimulation. Benzodiazepine receptor agonists have been found to reduce epileptiform activities in foci, as well as to inhibit generalisation.

OFQ, an LC132 receptor agonist mentioned above, was injected intracerebroventricularly in mice and the animals evaluated in a test used to detect anxiolytic effects (operant conflict test, light-dark test; EXAMPLES 2 and 3). It was demonstrated in both test paradigms that OFQ exhibited anxiolytic effects. In addition, intracerebroventricularly injected OFQ was demonstrated to be active in an a mouse model of epilepsy (audiogenic seizure model; EXAMPLE 4) which predicts anticonvulsant effects in general, as well as antiepileptic action in patients. None of these potential therapeutic effects of OFQ are described in literature.

Preferred tests are described in EXAMPLES 1, 2, 3 and 4 below:

Determination of LC132 receptor agonist activity and inhibition of forskolin-stimulated cAMP accumulation (EXAMPLE 1) demonstrates OFQ inhibits forskolin-stimulated cAMP accumulation in CHO cells transfected with LC132 in comparison to untransfected CHO cells. OFQ inhibits forskolin-stimulated cAMP accumulation in CHO cells transfected with the LC132 receptor with a median effective concentration ($EC_{50}$) of 1.05±0.21 nM and a maximal effect of approximately 80% inhibition at 100 nM. It has no effect on untransfected cells. For determination of binding kinetics of OFQ to its receptor the radioligand [$^{125}$I]Tyr$^4$-orphanin was developed and characterised (Reinscheid et al., J. Biol. Chem. 271: 14163–14168, 1996). [$^{125}$I]Tyr$^{14}$-orphanin binds to membranes prepared from CHO cells expressing the LC132 receptor in a saturable and displaceable manner with a $K_d$ of 56.2±7.3 pM and a $B_{max}$ of about 200 fmol/mg protein. OFQ inhibits the binding of [$^{125}$I]Tyr$^{14}$-orphanin to the LC132 receptor with an inhibitory constant ($K_i$) of 0.19±0.02 nM (Reinscheid et al. (1996), loc. cit.).

The operant conflict test for anxiolytic effect (EXAMPLE 2) shows that OFQ (mean±sem=24.6±3.6) produces a nonsignificant reduction of unpunished responding compared to vehicle injection (mean±sem=36.3±7.4) indicative of minimal motor impairment. In contrast, OFQ (mean±sem=16.2±6.0) significantly ($P<0.05$) enhances punished responding compared to vehicle injection (mean±sem=4.3±1.6) indicative of an anxiolytic effect. This pattern of results is similar to that produced by the marketed anxiolytic compound diazepam orally administered to these same two groups of mice, indicating the potential of OFQ as an anxiolytic drug in patients.

The light-dark box task for anxiolytic effect (EXAMPLE 3) shows that OFQ significantly ($P$'s$<0.05$) increases the time spent in the illuminated box at the doses 0.3 nmol/mouse (mean±sem=54±14 sec) and 1 nmol/mouse (mean±sem=58±19 sec) as compared to vehicle injection (mean±sem=11±5 sec). It also significantly ($P$'s$<0.05$) decreases the number of transition attempts at the doses 0.3 nmol/mouse (mean±sem=1.2±0.6), 1 nmol/mouse (mean±sem=0.7±0.2), and 3 nmol/mouse (mean±sem=0.4±0.3) as compared to vehicle injection (mean±sem=3.0±0.5). This pattern of results is indicative of the anxiolytic activity of OFQ.

The audiogenic seizure model (EXAMPLE 4) shows that OFQ exhibited a protective effective against acoustically induced tonic seizures in genetically sound sensitive mice with an $ED_{50}$ dose of 0.7 nmol/mouse. This result predicts the therapeutic value of OFQ in epilepsy and in reducing convulsions.

Accordingly, the present invention also relates to compounds obtainable by a method described above, e.g. OFQ and its derivatives and to the pharmaceutical compositions comprising one or more of these compounds and a therapeutically inert carrier material. In addition, the invention relates to the use of these compounds in the manufacture of a composition for the treatment of psychiatric and/or neurological disorders and to methods for treatment of psychiatric and/or neurological disorders comprising administering a therapeutically effective amount of OFQ or a derivative thereof. Examples for psychiatric and/or neurological are epilepsy, anxiety or convulsions.

The term "OFQ and its derivatives" refers to the peptide F-G-G-F-T-G-A-R-K-S-A-R-K-L-A-N-Q (SEQ ID NO: 1), to fragments and/or to non-naturally occurring peptides or mutants thereof. These kind of derivatives are peptides in which one or more of the amino acids of the natural OFQ peptide or its fragments have been replaced or deleted without loss of the agonist activity. Such derivatives may be produced by known methods of peptide chemistry.

The term "OFQ and its derivatives" also comprises derivatives which may be prepared from the functional groups occurring as side chains on the residues or the N- or C-terminal groups, by means known in the art, and are included in the invention as long as they remain pharmaceutically acceptable, i.e. they do not destroy the agonist activity of the peptides and do not confer toxic properties on compositions containing it. These derivatives may include, for example, polyethylene glycol side-chains which may mask antigenic sites and/or extend the residence of the OFQ peptide derivatives in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl- or threonyl residues) formed with acyl moieties.

The term "OFQ and its derivatives" also includes soluble forms of the above derivatives. Soluble forms may be prepared by methods known in the art, e.g. by chemical synthesis.

The dose ranges for the administration of OFQ and its derivatives may be determined by those of ordinary skill in the art without undue experimentation. In general, appropriate dosages are those which are large enough to produce the desired effect. The dosage should not be so large as to cause adverse side effects, such as unwanted cross-reactions, anaphylactic reactions, and the like. Generally, the dosage will vary with the age, condition, sex and extent of disease in the patient, counter indications, if any, immune tolerance and other such variables, to be adjusted by the individual physician. The expected dose range is about 0.1 ng/kg/day to about 0.1 mg/kg/day. The OFQ peptide and derivatives thereof can be administered parenterally by injection or by gradual perfusion over time. They can be administered intravenously, intraperitoneally, intramuscularly, or subcutaneously.

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See, generally, *Remington's Pharmnaceittical Science*, 18th Ed., Mack Eds., 1990.

The present invention also relates to compounds obtainable by a method described above and to the pharmaceutical compositions comprising one or more of these compound and a therapeutically inert carrier material.

Further, the invention comprises the use of the LC132 receptor for the screening of compounds useful for the treatment of psychiatric and/or neurological disorders, especially for the treatment of anxiety, epilepsy and convulsions as described above.

The following EXAMPLES are intended to illustrate details of the invention, without thereby limiting it in any manner.

EXAMPLES

EXAMPLE 1

Determination of LC132 Agonist Activity and Inhibition of Forskolin-stimulated cAMP Accumulation For determination of concentrations of cAMP, LC132 receptor transfected CHO cells or CHO dhfr- (wild type) cells were plated in 24-well plates and grown to confluency. After removal of the culture medium, test compounds or peptides dissolved in a total volume of 0.2 ml Dulbecco's Modified Eagle Medium containing 10 mM HEPES (pH 7.4), 1 mM forskolin and 1 mM D,L-4-(3-butoxy-4-methoxybenzyl)-2-imidazolidinone (obtainable from RBI) were added and the cells were incubated for 10 min at 37° C. Reactions were stopped by addition of 0.5 ml ice-cold ethanol and plates were frozen at −80° C. for 12 hours. After centrifugation of the plates, portions of the supernatant were removed and dried for cAMP determination. cAMP assays (Biotrak SPA, Amersham) were done according to the manufacturer's instructions. Ligand binding assays were done in 96-well deep bottom microwell plates. CHO cells stably expressing the LC132 receptor were harvested and resuspended in 10 volumes of binding buffer containing 50 mM Tris-HCl (pH 7.8), 5 mM $MgCl_2$, 1 mM EGTA, 0.1% BSA, and 0.1 mg/ml each of aprotinin, leupeptin and pepstatin. Membranes were prepared using a tissue homogenizer (setting 4 for 30 sec; PT20, Kinematica, Lucerne, Switzerland). Total membrane particulate was obtained after centrifugation at 45,000×g for 10 min at 4° C. The resulting pellet was resuspended and centrifuged twice as described above. Membranes were finally diluted in an appropriate volume of binding buffer and stored at −70° C. Protein concentration was determined using a BCA Protein Assay Kit (Pierce). Incubation of membranes (10–18 μg protein) with $[^{125}I]Tyr^{14}$-orphanin was performed at room temperature for 1 hour in a total volume of 200 μl binding buffer. For competition binding experiments 50,000 cpm of $[^{125}I]Tyr^{14}$-orphanin (62.5 pM) were added together with the indicated concentrations of unlabelled peptides. Non-specific binding was determined in the presence of 50 nM OFQ. Bound and free ligand were separated by rapid vacuum filtration through Whatman GF/C filters using a Brandel multichannel harvester. GF/C filters had been pretreated with 0.3% polyethylenimine containing 0.1% BSA for 1 hour at room temperature. Filters were washed six times with 1 ml ice-cold 50 mM Tris-HCl, pH 7.5 and then counted in a gamma counter.

EXAMPLE 2

Operant Conflict Test for Anxiolytic Effect

Female albino mice (Ibm: MORO (SPF); Biological Research Labs, Füllinsdorf, Switzerland) were used. At the start point of this experiment these mice were at least 2–3 month old and had previously been well trained in the operant conflict task. The mice were individually housed in Macrolon® type plastic cages (circa 13×23×13 cm) with sawdust bedding. Room temperature and humidity were regulated in animal quarters maintained on a natural light-dark cycle. Tap water was available ad libitum, whereas access to the standard laboratory chow was restricted. The mice were maintained at approximately 80–85% of their free feeding body weight. The training and testing procedures are provided by Martin et al. (Pharmacol. Biochem. Behav. 46: 905–910, 1993): Food-deprived mice were well trained in a task in which during the initial 5 minutes each time a lever was pressed (unpunished responding) a food reward was automatically delivered and then during the subsequent 15 minutes each lever-press produced (punished responding) food reward, but concomitantly a mild foot-shock was given. Consistent with the published literature, oral administration of 10 mg/kg diazepam 30 minutes prior to testing resulted in some reduction of unpunished responding but enhanced punished lever-pressing in these mice. Two groups (N's =9) were formed. The volume of intracerebroventricular injection was 2 µl. The vehicle was artificial cerebrospinal fluid. OFQ (Research Genetics, Inc., Huntsville, Ala.) was given at the dose 3 nmol/mouse. Both unpunished (i.e., the initial 5-min period of a conflict test) and punished (i.e., the subsequent 15-min period of a conflict test in which lever pressing resulted in food and concomitant shock) portions of a conflict test were evaluated. The technician carrying out the behavioral evaluation was blind (uninformed) to the treatment conditions for the individual animals. Statistical analysis was done comparing the two treatment groups using a Mann-Whitney U test with a p-value less than 0.05 accepted as statistically significant.

EXAMPLE 3

Light-dark Box Task for Anxiolytic Effect

Male albino mice [Ibm: MORO (SPF); Biological Research Labs, 4414 Füllingsdorf, Switzerland] were used. The mice were housed in group cages with sawdust bedding in the laboratory quarters for several days prior to testing. Room temperature and humidity were regulated and the animal quarters were maintained on a reversed light-dark cycle. Tap water and standard laboratory chow was available ad libitum. Exploratory activity in a light-dark box task was determined in naive mice. The apparatus consisted of one opaque and one transparent Plexiglas® boxes of equal size (20×20×14 cm) connected by an opaque plastic tunnel (5×7×10 cm). The transparent box was illuminated (4400 lux at the center of this box). Five minutes after intracerebroventricular injection, a mouse was placed in the tunnel facing the dark box. The time spent in the illuminated box, the number of transition attempts (only the head and forepaws entered into the lighted box), and the number of completed transitions from the opaque box to the transparent box were recorded for the 5-minute session. A mouse was judged to have changed compartments when all four paws were placed in the next compartment. The floor was thoroughly cleaned after each test. Each treatment group was composed of 10–20 mice. The volume of the intracerebroventricular injection was 2 µl. OFQ (Research Genetics, Inc., Huntsville, Ala.) was given at the doses 3, 1, 0.3 and 0.1 nmol/mouse. Artificial cerebrospinal fluid was used as the vehicle. The technician carrying out the behavioral evaluation was blind (uninformed) to the treatment conditions for the individual animals. Differences between the treatment groups were evaluated with the Student's t-test with a p-value $\leq 0.05$ accepted as statistically significant.

EXAMPLE 4

Audiogenic Seizure Model for Antiepileptic/anticonvulsant Effects

Young mice [DBA/2J (SPF); Biological Research Labs, 4414 Füllinsdorf, Switzerland] were used. The mice were housed in group cages with sawdust bedding in the laboratory quarters prior to testing. Room temperature and humidity were regulated and the animal quarters were maintained on a natural light-dark cycle. Tap water and standard laboratory chow was available ad libitum. Protection from audiogenic seizures was investigated in naive 3-week-old DBA/2J mice (which are known to be genetically seizure susceptible). Additional experimental details are provided elsewhere (Martin et al., Psychopharmacology 111: 415–422, 1993) In short, immediately after intracerebroventricular injection, each mouse was placed in a separate open transparent Plexiglass® box (21×44×21 cm) containing sawdust bedding. Testing was done is a sound-isolated chamber and involved exposure to a 14 kHz sinusoidal tone at 110 dB (zero dB was defined as a pressure level of 20 µPa) for 1 minute during which observations were made. Auditory stimulation was given 5 minutes after treatment. Groups of 8 mice were used to evaluate each dose and the vehicle condition. The volume of the intracerebroventricular injection was 2 µl. OFQ (Research Genetics, Inc., Huntsville, Ala.) was given at the doses 10, 3, 1, 0.1, and 0.01 nmol/mouse. Artificial cerebrospinal fluid was used as the vehicle. The technician carrying out the behavioral evaluation was blind (uninformed) to the treatment conditions for the individual animals. The proportion of the group failing to exhibit tonic convulsions was recorded. The $ED_{50}$ value was calculated with probit analysis.

---

What is claimed is:

1. A method of identifying a compound having antiepileptic or anticonvulsant activity, comprising:
   (a)(i) contacting a native LC132 receptor with a candidate compound;
   (ii) detecting induction of LC132 agonist activity by the candidate compound, wherein the LC132 agonist activity is inhibition of forskolin-stimulated cAMP accumulation;
   (b)(i) testing the candidate compound from step (a)(ii) in an assay for antiepileptic or anticonvulsant activity; and
   (ii) detecting a positive result in the assay for antiepileptic or anticonvulsant activity, thereby identifying the compound having antiepileptic or anticonvulsant activity.

2. The method of claim 1 where in step (a) the LC132 receptor is present on the surface of a cell membrane.

3. The method of claim 1 wherein the assay for antiepileptic or anticonvulsant activity is the audiogenic seizure model.

4. The method of claim 1, wherein the native LC132 receptor is native human LC132 receptor.

5. A method of identifying a compound having anxiolytic activity comprising:
   (a)(i) contacting a native LC132 receptor with a candidate compound;
   (ii) detecting induction of LC132 agonist activity by the candidate compound, wherein the LC132 agonist activity is inhibition of forskolin-stimulated cAMP accumulation;
   (b) (i) testing the candidate compound from step (a)(ii) in an assay for anxiolytic activity; and
   (ii) detecting a positive result in the assay for anxiolytic activity, thereby identifying the compound having anxiolytic activity.

6. The method of claim 5 where in step (a) the LC132 receptor is present on the surface of a cell membrane.

7. The method of claim 5, wherein the native LC132 receptor is native human LC132 receptor.

8. The method of claim 5 wherein the assay for anxiolytic activity is the operant conflict test or the light-dark box task.

9. A method of identifying a compound having antiepileptic or anticonvulsant activity, comprising:
   (a)(i) contacting a native LC132 receptor with a candidate compound;
   (ii) detecting induction of LC132 agonist activity by the candidate compound, wherein the LC32 agonist activity is inhibition of forskolin-stimulated cAMP accumulation by an $IC_{50}$ value of less than 1 $\mu$M of the candidate compound;
   (b)(i) testing the candidate compound from step (a)(ii) in an assay for antiepileptic or anticonvulsant activity; and
   (ii) detecting a positive result in the assay for antiepileptic or anticonvulsant activity, thereby identifying the compound having antiepileptic or anticonvulsant activity.

10. A method of identifying a compound having anxiolytic activity comprising:
    (a)(i) contacting a native LC32 receptor with a candidate compound;
    (ii) detecting induction of LC132 agonist activity by the candidate compound, wherein the LC132 agonist activity is inhibition of forskolin-stimulated cAMP accumulation by an $IC_{50}$ value of less than 1 $\mu$M of the candidate compound;
    (b)(i) testing the candidate compound from step (a)(ii) in an assay for anxiolytic activity; and
    (ii) detecting a positive result in the assay for anxiolytic activity, thereby identifying the compound having anxiolytic activity.

* * * * *

UNITED STATES PATENT AND TRADEMARK OFFICE
CERTIFICATE OF CORRECTION

PATENT NO. : 6,326,156 B1
DATED : December 4, 2001
INVENTOR(S) : Olivier Civelli, James Richard Martin, Frederick Monsma, Jean-Luc Moreau, Hans-Peter Noathacker and Rainer Reinscheid It is certified that error appears in the above-identified patent and that said Letters Patent is hereby corrected as shown below:

<u>Column 14,</u>
Line 12, replace "LC32" with -- LC132 --
Line 23, replace "LC32" with -- LC132 --

Signed and Sealed this

Thirtieth Day of April, 2002

Attest:

Attesting Officer

JAMES E. ROGAN
*Director of the United States Patent and Trademark Office*